US00PP33661P2

(12) United States Plant Patent
Verhoef

(10) Patent No.: US PP33,661 P2
(45) Date of Patent: Nov. 23, 2021

(54) ***WEIGELA* PLANT NAMED 'TVP1'**

(50) Latin Name: *Weigela florida*
Varietal Denomination: TVP1

(71) Applicant: Gijsbertus Verhoef, Hazerswoude-Dorp (NL)

(72) Inventor: Gijsbertus Verhoef, Hazerswoude-Dorp (NL)

(73) Assignee: BERT VERHOEF BOOMKWEKERIJ B.V., Hazerswoude-Dorp (NL)

( * ) Notice: Subject to any disclaimer, the term of this patent is extended or adjusted under 35 U.S.C. 154(b) by 0 days.

(21) Appl. No.: 17/224,390

(22) Filed: Apr. 7, 2021

(51) Int. Cl.
*A01H 5/02* (2018.01)
*A01H 6/00* (2018.01)

(52) U.S. Cl.
USPC ..... Plt./226

(58) Field of Classification Search
USPC ..... Plt./226
CPC ..... A01H 5/02; A01H 6/00
See application file for complete search history.

*Primary Examiner* — Keith O. Robinson
(74) *Attorney, Agent, or Firm* — Penny J. Aguirre

(57) ABSTRACT

A new cultivar of *Weigela florida* plant named, 'TVP1', characterized by its compact and upright plant habit, its young foliage that is dark brown in color and mature foliage that is dark green in color, its glossy foliage, its leaves that are convex in aspect, its twigs and leaves with a pubescent surface, and its flower petals with outer surfaces light purple-pink in color and inner surfaces white in color with a yellow spot.

2 Drawing Sheets

Botanical classification: *Weigela florida.*
Variety denomination: 'TVP1'.

CROSS REFERENCE TO A RELATED APPLICATION

This application is related to a European plant breeders' rights application filed on Mar. 24, 2020, application No. 2020/0838. There have been no offers for sale anywhere in the world prior to the effective filing date of this Application and no accessibility to one of ordinary skill in the art could have been derived from the printed plant breeder's rights documents.

BACKGROUND OF THE INVENTION

The present invention relates to a new and distinct cultivar of *Weigela* and will be referred to hereafter by its cultivar name, 'TVP1'. 'TVP1' represents a new cultivar of *Weigela*, a deciduous shrub grown for landscape use.

The new cultivar is the result of a controlled breeding program conducted by the Inventor in Hazerswoude-Dorp, The Netherlands. The objective of the breeder program is to develop new cultivars of *Weigela* that are rich flowering with multi-colored flowers and compact and low growing plant habits. The Inventor made a cross in spring of 2015 between an unnamed proprietary plant in the Inventor's breeding program, reference no. BV010, as the female parent and *Weigela* 'Kolmagira' (U.S. Plant Pat. No. 20,384) as the male parent. 'TVP1' was selected as a single unique plant from the resulting seedlings of the cross in spring of 2017.

Asexual propagation of the new cultivar was first accomplished by softwood stem cuttings by the Inventor in June of 2018 in Hazerswoude-Dorp, The Netherlands. Asexual propagation by softwood stem cuttings has determined that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'TVP1' as a unique cultivar of *Weigela.*

1. 'TVP1' exhibits a compact and upright plant habit.
2. 'TVP1' exhibits young foliage that is dark brown in color and mature foliage that is dark green in color.
3. 'TVP1' exhibits glossy foliage.
4. 'TVP1' exhibits leaves that are convex in aspect.
5. 'TVP1' exhibits twigs and leaves with a pubescent surface.
6. 'TVP1' exhibits flower petals with outer surfaces light purple-pink in color and inner surfaces white in color with a yellow spot.

The female parent plant differs from 'TVP1' in having a broadly spreading plant habit and flower petals with a single color. The male parent plant differs from 'TVP1' in having variegated foliage and flower petals with a single color. 'TVP1' can be compared to the *Weigela florida* varieties 'Victoria' (not patented) and 'Samba' (not patented). 'Victoria' is similar to 'TVP1' in having dark colored foliage. 'Victoria' differs from 'TVP1' in having a less compact plant habit, less pubescence on the twigs and foliage, foliage that is darker in color, and flower petals that are red-purple in color on both surfaces. 'Samba' is similar to 'TVP1' in having dark foliage and a compact plant habit. 'Samba' differs from 'TVP1' in having a more compact plant habit, foliage that is darker in color, and flower petals that are red-purple in color on both surfaces.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by van Vliet New plants, Landshaft, dreamstime, and bestplant.

BRIEF DESCRIPTION OF THE DRAWINGS

The accompanying color photographs were taken in August and illustrates the overall appearance and distinct characteristics of 24-month-old plants the new *Weigela* as field in Hazerswoude-Dorp, The Netherlands.

The photograph in FIG. 1 provides an overall view of the growth habit of 'TVP1' in bloom.

Figure 1:
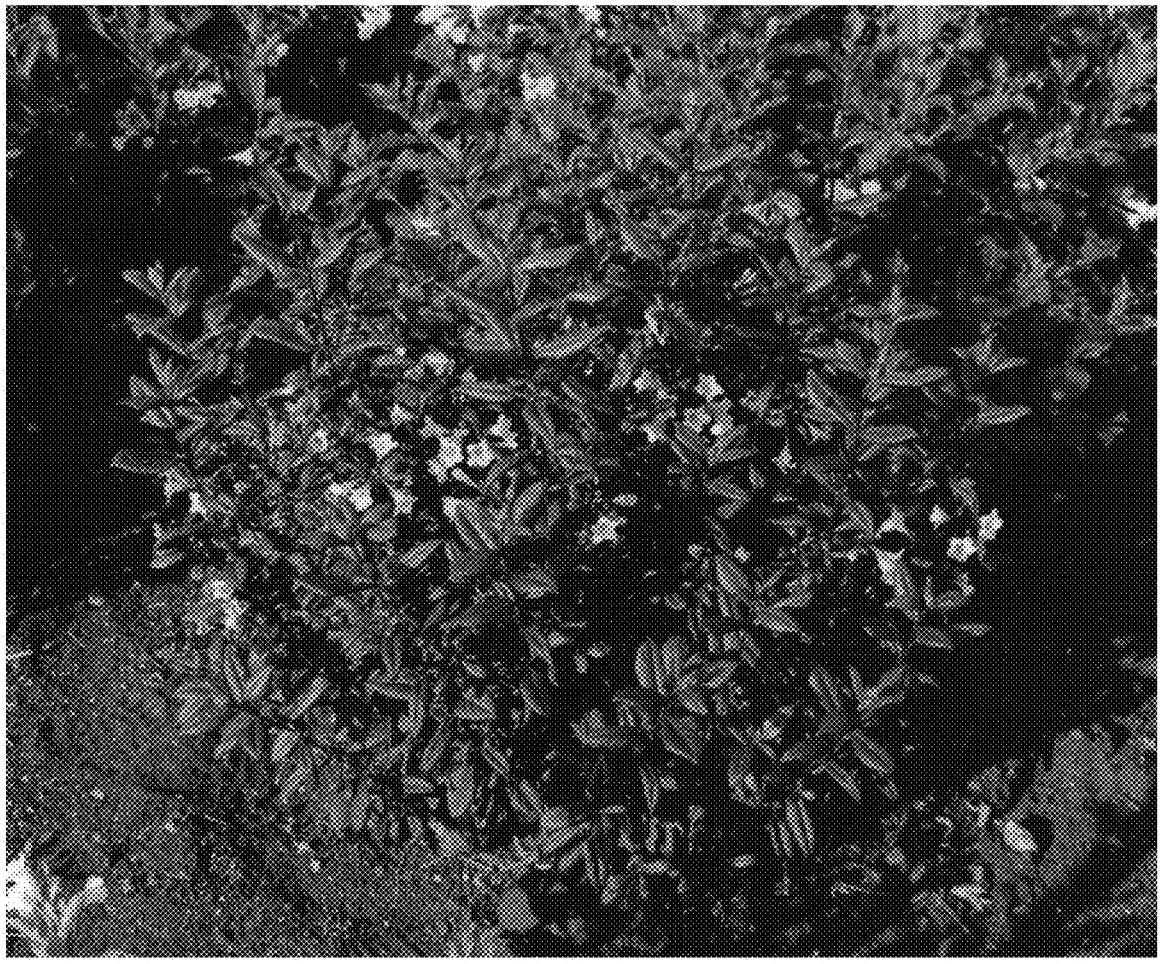
Figure 2:
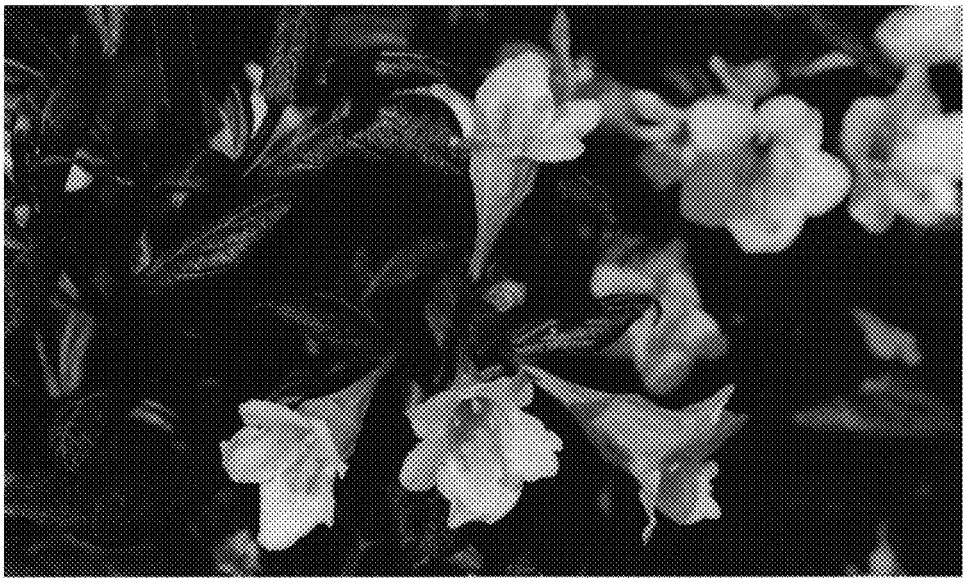

The photograph in FIG. 2 provides a close-up view of the flowers of 'TVP1'.

Figure 3:
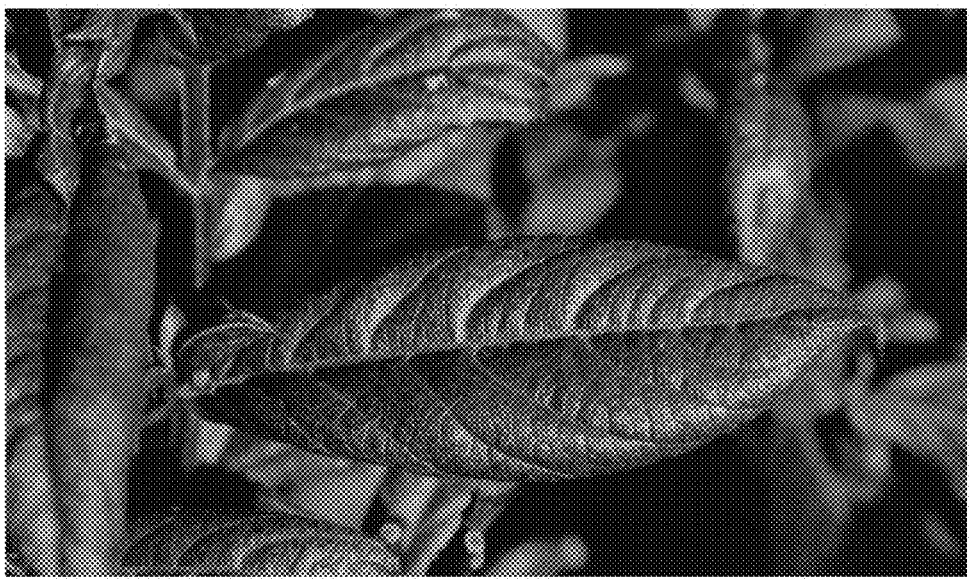

The photograph in FIG. 3 provides a close-up view of the foliage of 'TVP1'.

The colors in the photograph may differ slightly from the color values cited in the detailed botanical description, which accurately describe the colors of the new *Weigela*.

DETAILED BOTANICAL DESCRIPTION

The following is a detailed description of the new cultivar as observed on 24-month-old plants of *Weigela* 'TVP1' as field grown in Hazerswoude-Dorp, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Remontant; blooms from late spring (May) and fall (September into October) in The Netherlands.

*Plant type*.—Deciduous flowering shrub.

*Plant habit*.—Compact, upright and slightly spreading, freely branched.

*Plant size*.—Reaches about 74.3 cm in height and 82 cm in width as a 24-month-old plant and 100 cm in height and 125 cm in width as a mature plant in the landscape.

*Cold hardiness*.—At least in U.S.D.A. Zone 5.

*Diseases and pests*.—No susceptibility to resistance to diseases or pests has been observed.

*Root description*.—Fibrous, moderately dense.

*Propagation*.—Softwood stem cuttings.

*Root development*.—An average of 6 weeks for root initiation and an average of 3 months to produce a young rooted plant.

*Growth rate*.—Moderate to high.

Branch description:

*Branch shape*.—Slightly quadrangular.

*Branch color*.—New and mature; N186C, bark; N186C, axially striped 197C.

*Branch size*.—An average of 49 cm in length and 5 mm in diameter.

*Branch surface*.—New growth (twigs); slightly glossy, moderately to densely covered with short hairs an average of 1 mm in length and 156A in color.

*Branch aspect*.—Upright to outward at an average angle of 35°.

*Branch strength*.—Moderately strong.

*Branching*.—An average of 40 main basal branches and 4 lateral branches per main branch.

*Internode length*.—Average of 3.6 cm.

Foliage description:

*Leaf shape*.—Obovate.

*Leaf division*.—Simple.

*Leaf base*.—Attenuate.

*Leaf apex*.—Apiculate.

*Leaf fragrance*.—None.

*Leaf aspect*.—Slightly carinate, convex.

*Leaf venation*.—Pinnate, color upper surface 177B, color lower surface 195A, changing to 177B.

*Leaf margins*.—Serrate, moderately rev olute.

*Leaf arrangement*.—Opposite or in whorls of three.

*Leaf attachment*.—Petiolate.

*Leaf surface*.—Both surfaces glossy and slightly rugose, upper surface sparsely pubescent with very short hairs, average of 0.3 mm in length, 156A in color, lower surface densely pubescent with short hairs; an average of 0.75 mm in length, 156A in color.

*Leaf size*.—An average of 6.7 cm in length and 3.8 cm in width.

*Leaf quantity*.—An average of 10 per lateral branch.

*Leaf color*.—Young upper surface 200B, young lower surface 200C, mature upper surface 147A, tinged 200B, mature lower surface 147A, margins tinged 200B.

*Petioles*.—Average of 3 mm in length, 2 mm in width, upper surface color 177A lower surface color 177B, both surfaces are matte and densely covered with soft pubescence 0.5 mm in length and 156A in color.

*Stipules*.—None.

Inflorescence description:

*Inflorescence type*.—Solitary, in pairs, or in small clusters at terminus and leaf axils.

*Inflorescence size*.—Average of 4.4 cm in height and 6.8 cm in diameter.

*Flower buds*.—Oblanceolate in shape, an average of 1.8 cm in length and 5 mm in diameter, color; 184B, lower part of bud 145B, matte surface.

*Flower fragrance*.—None.

*Lastingness of flowers*.—About 12 days, self-cleaning.

*Flower aspect*.—Outward to slightly upright.

*Flower quantity*.—An average of 7 per inflorescence, 600 buds and flowers per plant.

*Flower type*.—Tubular.

*Flower size*.—Average of 2 cm in height and diameter, 3.3 cm in depth, throat; 1 cm in diameter, tube; 2.4 cm in length, 9 mm in diameter.

*Peduncles*.—Average of 2 cm in length, 1.25 mm in diameter, held in a 20° angle to lateral branch axis, strong, densely covered with soft pubescent hairs, an average of 0.5 mm in length, 156A in color, matte surface, ranging between N186C and 200A in color.

*Calyx*.—Rotate in shape, an average of 8 mm in depth and 4 mm in width.

*Sepals*.—5, rotate, linear in shape, acute apex, cuneate base, entire margin, an average of 8 mm in length and 1 mm in width, lower 30% fused, color; when opening and fully open upper and lower surface 177A, upper surface smooth and glabrous, lower surface smooth, very sparsely covered with short hairs an average of 0.2 mm in length and too small to measure color, both surfaces slightly glossy.

*Petals.*—5, lower 75% fused into tube, spathulate in shape, margin entire on free portion, apex obtuse, an average of 3.2 cm in length, 9 mm in width, both surfaces non-rugose, inner surface matte, glabrous, slightly velvety, outer surface matte, glabrous, non-velvety, color; when opening and fully open inner surface 155D with spot of one petal 13B, when opening and fully open outer surface 185D with margins NN155A.

Reproductive organs:

*Gynoecium.*—Pistil; 1, average of 2.9 cm in length, style; average of 2.7 cm in length, and 182C in color, stigma; club-shaped, 1.5 mm in length and 2 mm in diameter, 156D in color, ovary; 200B in color.

*Androecium.*—Stamens; 5, filaments; N155A, fading towards the base to 186D in color and an average of 7 mm in length, anthers; 159A in color, an average of 3 mm in length, 0.5 mm in width, narrowly oblong in shape, pollen; moderate in quantity and 158D in color.

*Fruit and seed.*—No fruit or seed production has been observed.

It is claimed:

1. A new and distinct cultivar of *Weigela* plant named 'TVP1' as herein illustrated and described.

* * * * *